(12) United States Patent
Bach et al.

(10) Patent No.: US 8,870,838 B2
(45) Date of Patent: Oct. 28, 2014

(54) OSTOMY COLLECTING DEVICE

(75) Inventors: Anders Bach, Copenhagen (DK); Esben Stroebech, Hoersholm (DK); Mads Lykke, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 335 days.

(21) Appl. No.: 12/737,314

(22) PCT Filed: Jul. 16, 2009

(86) PCT No.: PCT/DK2009/050182
§ 371 (c)(1),
(2), (4) Date: Dec. 29, 2010

(87) PCT Pub. No.: WO2010/006622
PCT Pub. Date: Jan. 21, 2010

(65) Prior Publication Data
US 2011/0098665 A1    Apr. 28, 2011

(30) Foreign Application Priority Data

Jul. 18, 2008   (DK) .................................. 2008 01019

(51) Int. Cl.
*A61F 5/445* (2006.01)
*A61F 5/443* (2006.01)
*A61L 24/00* (2006.01)

(52) U.S. Cl.
CPC ............. *A61F 5/443* (2013.01); *A61L 24/001* (2013.01)
USPC ...................................................... 604/339

(58) Field of Classification Search
CPC ..... A61M 1/0001; A61M 1/0013; A61F 5/44; A61B 10/007
USPC ................. 604/317, 304–308, 277, 327, 331, 604/336–338, 341, 343, 344, 355, 525; 602/58; 427/208.8
See application file for complete search history.

(56) References Cited

U.S. PATENT DOCUMENTS

| 3,029,814 A | * | 4/1962 | Kravitz ............................ 602/67 |
| 4,846,829 A | * | 7/1989 | Lloyd ............................ 604/389 |
| 5,230,701 A | | 7/1993 | Meyer et al. |
| 5,423,783 A | * | 6/1995 | Battles et al. .................. 604/344 |
| 5,571,080 A | * | 11/1996 | Jensen ............................ 602/56 |
| 5,858,150 A | * | 1/1999 | Yarusso et al. ................. 156/163 |
| 6,248,915 B1 | | 6/2001 | Ito et al. |
| 6,730,397 B2 | * | 5/2004 | Melancon et al. ......... 428/355 R |
| 2001/0051182 A1 | * | 12/2001 | Hopp ............................ 424/449 |
| 2006/0184145 A1 | * | 8/2006 | Ciok et al. ..................... 604/338 |
| 2008/0311396 A1 | | 12/2008 | Hamada et al. |
| 2010/0191204 A1 | | 7/2010 | Bach et al. |

FOREIGN PATENT DOCUMENTS

| CN | 101754776 A | | 6/2010 |
| EP | 0 674 890 A2 | | 10/1995 |
| EP | 674890 A2 | * | 10/1995 |
| JP | 2004 067720 A | | 3/2004 |
| WO | WO 02/066087 A1 | | 8/2002 |
| WO | WO 2005/032401 | | 4/2005 |
| WO | WO 2008/074333 A1 | | 6/2008 |

OTHER PUBLICATIONS

Bird, R.B., et al., "Dynamics of Polymeric Liquids," Wiley-Interscience Publication, vol. 1, sec. ed., 1987, pp. 112-117.

* cited by examiner

*Primary Examiner* — Melanie Hand
*Assistant Examiner* — Ned T Heffner
(74) *Attorney, Agent, or Firm* — Coloplast Corp., Coloplast A/S; Nick Baumann

(57) ABSTRACT

An ostomy collecting device for attachment to the body comprising a collecting pouch and an adhesive wafer, the wafer comprises a soft adhesive layer and a backing layer wherein the wafer is more stretchable in a first direction than in a second direction. The anisotropic nature of the wafer facilitates a flexible wafer during use and secures easy removal.

21 Claims, No Drawings

OSTOMY COLLECTING DEVICE

This is a national stage of PCT/DK09/050,182 filed Jul. 16, 2009 and published in English, which claims the priority of Denmark number PA 2008 01019 filed Jul. 18, 2008, hereby incorporated by reference.

BACKGROUND OF THE INVENTION

1. Field of the Invention

The present invention relates to an ostomy collecting device for attachment to human skin.

2. Description of the Related Art

Collecting devices for collecting bodily waste, ostomy appliances, wound or fistulae drainage bandages or devices for collecting urine are usually in the form of a receptacle, e.g. a bag, pouch or tube for receiving the waste, connected to an adhesive wafer that can be attached to the skin of the patient. The wafer is typically in the form of a backing layer coated on the skin-facing surface with an adhesive layer and the wafer may further be provided with an aperture for accommodating the body opening. The size and shape of said aperture can often be adapted individually to fit the anatomy of the patient.

For many medical applications safe adhesion is often the most important property in a given device, for example for ostomy devices, which are placed on the abdominal skin. Hence, traditionally fairly aggressive, absorbing and high modulus adhesives are used in combination with a robust high modulus backing to facilitate the anchorage and removal of the device. While it is possible to produce devices with very good and safe adhesion and a reasonable easy removal without excessive stretching in this way, the carry comfort is limited due to the rigid and stiff system, which tends to stress the abdominal skin and produces a "plate like" feel during use.

Ostomy devices, applied on the abdomen of a user, are exposed to quite severe stress during the movements of the user. Especially, in vertical direction, e.g. when the user is bending or stretching the wafer is affected. Abdominal skin has high flexibility, especially in vertical direction where a deformation up to 40% is seen during bending and stretching. In horizontal direction such high deformations are not seen.

It has been discovered that with a combination of a low modulus adhesive and corresponding low modulus backing layers, devices can be produced, which are very comfortable to wear and which both have very good and safe adhesion due to the soft adhesive and low modulus enabling the wafer to follow the movements of the body.

However, a drawback of these appliances is that they, due to the low modulus, are difficult to remove as they will stretch and elongate during detachment.

SUMMARY OF THE INVENTION

It is an object of an embodiment of the invention to provide an ostomy device that is soft and flexible and able to follow the movements of the skin and yet easy to detach from the skin. This is achieved by introducing anisotropy into the adhesive wafer, in a way that the wafer is more stretchable in the vertical direction of the user than in the horizontal direction, and thus is easily detachable when peeled in a specific direction.

DETAILED DESCRIPTION OF THE INVENTION

In an embodiment of the invention, an ostomy collecting device for attachment to the body comprises a collecting pouch and an adhesive wafer, the wafer comprising a soft adhesive layer and a backing layer and the wafer being more stretchable in a first direction than in a second direction.

It has now been discovered that a soft ostomy device with high adhesion, high degree of wearer comfort and minimal stretching during removal, can be obtained using an anisotropic device construction. The adhesive wafer of the device according to the invention has a low modulus in a first direction and a higher modulus in a second direction.

Typically, in anisotropic materials, the direction of highest modulus is perpendicular to the direction of the lowest modulus. In these cases, the low modulus direction is applied in the direction where the most stretching and bending occurs, allowing the skin of the user to move relatively freely and simultaneously protecting the device against high stresses, which may result in unintended detachment and failure. The high flexibility ensures a high comfort for the user during the wear of the device. Thus, the high modulus direction is applied substantially perpendicular to the stretch direction, hence causing the least discomfort to the wearer and putting the least stress on the device yet allowing the device to be removed in the direction with reduced stretching of the wafer during peel.

In anisotropic layers made of woven fabric, the direction of lowest modulus is in the bias direction. This direction is in a 45° angle to the directions of highest modulus, which are in the warp and weft directions. When e.g. using a woven fabric as anisotropic layer, the soft bias direction should be in the vertical direction of the user when standing up. Again, in this way the softest direction in the fabric is in the direction of the user where he or she will do the most stretching of the skin.

The adhesive of the wafer is soft in order for the total wafer to be able to stretch. By soft adhesive layer is meant an adhesive with a complex modulus G* as defined herein of less than 50 kPa measured at 32° C. and 1 Hz.

In a preferred embodiment, the soft adhesive has a complex modulus G* of less than 20 kPa measured at 32° C. and 1 Hz.

Herein, we define the first direction in the wafer as the direction of lowest tensile modulus and the second direction as the direction of highest modulus. The two directions are usually perpendicular to each other, but can in some cases, e.g. when using woven fabrics be in a 45° angle to each other.

By anisotropic is understood that the material is exhibiting tensile properties with different values when measured in different directions, in this case a lower force is needed to stretch the material (wafer, film and/or adhesive) in a first direction than in a second direction. Herein, is meant that the wafer is anisotropic when the average tensile force in the first direction is less than 90% of the average tensile force in the second direction at 10% strain. More preferred, the wafer is anisotropic when the average tensile force in the first direction is less than 80% of the average tensile force, even more preferred less than 50% in the second direction at 10% strain.

The device is especially well suited for ostomy applications where the demand for adhesion and safe anchorage of the device is extreme. To secure the device safely, adhesives for ostomy devices are typically fairly aggressive which results in a relative high peel force. For soft comfortable devices, a high peel force may cause excessive and unwanted stretching when the device is removed. Using a device according to the current invention solves this problem.

The device of the invention is well suited for applications where the device is to be fixated to a body part with a high degree of skin movement, for example abdominal skin.

By providing the wafer with anisotropic properties, it is surprisingly possible to obtain a device being highly flexible and stretchable is one direction and yet easy to remove when peeled from a second direction where the stretchability of the wafer is more limited.

In a preferred embodiment, the average tensile force at 20% is less than 2 N/2.5 cm in the first direction and the average tensile force at 10% is less than 3 N/2.5 cm in the second direction.

It is preferred that the first direction is substantially perpendicular to the second direction. By substantially perpendicular is meant that the angle between the first and the second direction is between 80 and 100 degrees. The orientation is preferably such that the first direction is vertical when applied to the abdomen of a standing user, thus providing the device with maximum stretch in the bending vertical direction and low stretch in the horizontal direction facilitating easy removal without excess stretching if peeled in the high modulus cross direction. The wafer may be provided with markings signalling the optimal peel direction. The marks may be in the form of visual marks and/or they may be in the form of e.g. depressed or raised ribs or knobs on the non-skin facing surface of the wafer.

The anisotropic properties of the wafer may be achieved by providing one or more of the components of the wafer with the desired properties. In a preferred embodiment of the invention, the wafer may comprise an anisotropic layer.

An anisotropic layer may be incorporated in the adhesive layer or it may be located between the backing layer and the adhesive layer. In one embodiment of the invention, the anisotropic layer is located on the non-skin facing surface of the backing layer.

In an embodiment of the invention, the adhesive is anisotropic. The properties may e.g. be provided to the adhesive by way of application or by incorporating fibres, non-woven or a film layer.

In a preferred embodiment of the invention, the backing layer is anisotropic.

Anisotropic films or fabrics are well known. The anisotropic layer may be a film, woven, non-woven, fibre, knit, fabric, textile, laminate or foam or combinations thereof.

The backing layer of the device of the present invention is preferably in the form of a polymer film, coating, laminate, textile or non-woven. The backing layer is preferably a highly flexible film, being strong enough for attachment of e.g. couplings and/or pouch and for removing the device in one piece, but soft enough to follow the movements of the body.

In one embodiment, the backing layer is a polyurethane film optionally a laminate or a co-extruded film.

Preferably, the backing layer has thermoplastic elements that enable welding of e.g. a pouch or coupling ring to the adhesive wafer. Preferred thickness of the backing layer is between 15-60 μm in order to maintain the softness of the adhesive wafer.

According to one embodiment, the backing layer is a multi layer film. Each layer in the film gives special properties to the backing layer. A thin weldable layer ensures good joining to the bag or coupling and a thicker soft layer ensures the mechanical properties. In one embodiment of the invention, the backing layer is impermeable to vapour.

The adhesive of the wafer may be any suitable soft adhesive. Preferred adhesives are soft gel adhesives, such as silicone or polyurethane adhesives. An especially preferred adhesive is a polyalkyleneoxide polymer and organosiloxane based cross-linked adhesive system.

In a preferred embodiment of the invention, the adhesive comprises ethylene vinyl acetate.

The adhesive comprising ethylene vinyl acetate may suitably be an adhesive known in the art such as the adhesive composition disclosed, for example in Danish patent application PA 2007 01003.

In a preferred embodiment of the invention, the adhesive comprises polyacrylate.

In a preferred embodiment of the invention, the adhesive wafer comprises the combination of an adhesive comprising a polyalkyleneoxide polymer and organosiloxane based cross-linked adhesive system and a low modulus backing layer. The soft construction facilitates easy adaptation to scars, irregularities and skin-folds. The device may be removed with minimal pain due to extreme flexibility and no skin cells are stripped off and thus no traumatisation of the skin occurs. The soft adhesive has a broad peel front and good tenancy during use. Reposition of the adhesive is also possible without loss of tack.

The adhesive layer may be moisture absorbent. The absorbency of the adhesive may be achieved by incorporating absorbent material in the adhesive, e.g. in the form of absorbent particles or salt.

The adhesive layer of the device of the invention may in a preferred embodiment of the invention comprise a polyalkyleneoxide polymer and organosiloxane based cross-linked adhesive system.

According to one embodiment of the invention the adhesive layer of the wafer comprises the reaction product of:
 (i) a polyalkyleneoxide polymer having one or more unsaturated end groups and
 (ii) an organosiloxane comprising one or more Si—H groups, carried out in the presence of an addition reaction catalyst.

According to another embodiment of the invention, the adhesive composition of the device comprises more than 90% w/w of the polyalkylene oxide polymer that consists of polymerised alkyleneoxide moities having three or more carbon atoms.

According to another embodiment of the invention, the adhesive composition of the device comprises the reaction product of:
 (i) a polyalkyleneoxide polymer having at least two unsaturated end groups and wherein more than 90% w/w of the polyalkylene oxide polymer consists of polymerised alkyleneoxide moities having three or more carbon atoms,
 (ii) a polysiloxane cross-linking agent comprising 3 or more Si—H groups and optionally
 (iii) a polysiloxane chain extender comprising up to 2 Si—H groups carried out in the presence of an addition reaction catalyst.

According to a preferred embodiment of the invention, the addition reaction catalyst is a Pt vinyl siloxane complex.

According to a preferred embodiment of the invention, the polyalkylene oxide polymer is polypropyleneoxide.

According to a further preferred embodiment of the invention, the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention, the polyalkylene oxide polymer is polypropyleneoxide.

The polypropylene oxide having unsaturated end groups may be a compound of formula $$CH_2=C(R^1)-(Z)-O-(X)_n-(W)-C(R^2)=CH_2 \quad (Ia)$$

or $$CH(R^1)=CH-(Z)-O-(X)_n-(W)-CH=CH(R^2) \quad (Ib)$$

wherein $R^1$ and $R^2$ are independently selected from hydrogen and $C_{1-6}$-alkyl;

Z and W is $C_{1-4}$-alkylene;

X is $-(CH_2)_3-O-$ or $-CH_2-CH(CH_3)-O-$; and n is 1-900, more preferred 10-600 or most preferred 20-600.

The number average molecular weight of the polyalkylene oxide having unsaturated end groups is suitably between 500 and 100.000, more preferred between 500 and 50.000 and most preferred between 1.000 and 35.000.

Polypropylene oxide having unsaturated end groups may be prepared as described in U.S. Pat. No. 6,248,915 and WO 05/032401 or analogously to the methods described therein. Other polyalkylene oxide polymers may be prepared analogously.

The polysiloxane cross-linking agent comprising 3 or more Si—H groups is suitable a compound having the formula $$R-SiO(R,R)-(SiO(R,R))_m-Si-(R,R,R) \quad (II)$$

wherein at least three of the groups R are hydrogen and the rest of the groups R are each independently selected from $C_{1-12}$-alkyl, $C_{3-8}$-cycloalkyl, $C_{6-14}$-aryl and $C_{7-12}$-arylalkyl; and m is 5-50, or preferably 10-40. The number average molecular weight as determined by GPC is suitably 500-3.000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula $$R^3-SiO(R^3,R^3)-(SiO(R^3,R^3))_m-Si-(R^3,R^3,R^3) \quad (III)$$

wherein up to 2 of the groups $R^3$ are hydrogen and the rest of the groups $R^3$ are each independently selected from $C_{1-12}$-alkyl, $C_{3-8}$-cycloalkyl, $C_{6-14}$-aryl and $C_{7-12}$-arylalkyl; and m is 0-50. The number average molecular weight as determined by GPC is suitably between 200 and 65.000, most preferably between 200 and 17.500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the $-(SiO(R^3,R^3))_m-$ chain of the compound of formula (II).

The polysiloxane cross-linking agent and the chain extender may be prepared as described in Japanese Patent Application No. 2002-224706 and WO No. 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, thus forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxanes and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The adhesive composition of the device according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers and surfactants. The adhesive may also comprise pharmaceutically active ingredients. These optional ingredients may be present in the reaction mixture during the cross linking reaction.

It may be advantageous that the adhesive comprises absorbent particles. The particles may be absorbent articles such as mineral salt, hydrocolloid, microcolloids or super absorbers in order for the adhesive to absorb moisture from skin.

Preferred particle size of the absorbent particles is smaller particles, as they are more difficult to see by the naked eye and will give products that are more pleasing to the eye. An upper limit on particle size is the size of the smallest dimension of the adhesive. Thus, a 300 µm thick adhesive should not contain particles with diameters above 300 µm. There is a tendency of the hygroscopic particles to agglomerate and this effect will increase with decreasing particle size. Therefore, a preferred particle size would be from 10-300 μm. Also, the particles may contain an anti agglomerating agent to reduce agglomeration of small particles.

Microcolloid particles are well known in the art e.g. from International Patent Application No. WO 02/066087, which discloses adhesive compositions comprising microcolloid particles. The microcolloid particles may have a particle size of less than 20 microns.

Salt may be advantageous to use as absorber if it is contained within an ion impermeable matrix like the hydrophobic adhesive used in the device of this invention. Some salts like sodium chloride have an equilibrium vapour pressure of about 75% at skin temperature and will absorb water from skin and output because of the difference in vapour pressure.

In an embodiment of the invention, the adhesive comprises particles of mineral salt. The salt may be present in an amount of 1-50% w/w, more preferred in an amount of 5-25%.

In one embodiment of the invention, the adhesive comprises non-absorbent particles, which presence may modify the rheologic properties of the adhesive.

The absorbent adhesive layer may comprise 1-40% w/w of hydrocolloid (HC), microcolloids or super absorbent particles (SAP) particles, more preferred 5-30% w/w particles.

The collecting pouch may be detachable from the adhesive wafer by a coupling system or the pouch and the wafer may be integrated with the wafer, e.g. by welding. The two versions are known as one piece or two-piece appliances for ostomy.

In order to avoid rolling up of the edge portion during wear, it may be advantageous to bevel the edge portion of the wafer.

Materials and Methods
Adhesive Wafer Softness

To measure tensile properties of the adhesive wafer, the testing guidelines from standard ISO527-1 were used. However, to accommodate the layered structures examined here, an average tensile force at x% strain was defined as the force needed to deform an equivalent 2.5 cm wide strip of the wafer x%. The value is reported in N/2.5 cm. 'Dog-bone' test specimens similar to the ones described in ISO 527-2 FIG. 1 but with different dimensions to accommodate the fact that some adhesive wafers are too small to be tested with ISO 527-1 were used. The test samples had a width b1 of narrow portion of 4 mm and Gauge length L0 was 10 mm. The thickness of the sample is irrelevant when measuring the average tensile force as defined above. Deformation or strain e was calculated as the deformation divided by the initial length L0 as described in ISO 527-1. The rate of deformation was set to 1 mm/s. Values should be reported as averages of at least 3 measurements.

Determination of G*

The parameter G* or complex modulus as defined in "Dynamics of polymeric liquids", Vol. 1, sec ed 1987, Bird, Armstrong and Hassager, John Wiley and Sons inc., may be used as a measure of the hardness of an adhesive. G* at 32° C. and 1 Hz may be measured as follows: A plate of the unfoamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C.

Determination of Water Absorption

In order to get better correlation between measured water absorption and actual performance in a humanlike environment, a modified version of the ISO 62 standard was used: Pieces of adhesive of 1×25×25 mm³ were fastened on a piece of glass using double sided adhesive and the constructs were immersed in saline water (0.9% NaCl in demineralised water) at 32° C. After 24 hours, the samples were removed and carefully dripped dry and weighed. The change in weight was recorded and reported as weight gain in percent of the original dry weight of the adhesive. In the following, we will call this value $w_{24h}$.

The invention claimed is:

1. An ostomy collecting device for attachment to the body comprising:
   (i) a collecting pouch, and
   (ii) an adhesive wafer defining a surface,
   wherein the adhesive wafer includes
       (a) a soft adhesive layer, and
       (b) a backing layer
   wherein the wafer is stretchable in a first direction that is parallel to the surface of the wafer and is also stretchable in a second direction that is parallel to the surface of the wafer, the wafer being more stretchable in the first direction than in the second direction and wherein the average tensile force of the wafer at 20% strain is less than 2N/2.5 cm in the first direction and the average tensile force of the wafer at 10% strain is less than 3N/2.5 cm in the second direction.

2. The device according to claim 1, wherein the first direction is substantially perpendicular to the second direction.

3. The device according to claim 1 wherein the first direction is in an angle of 45 degrees to the second direction.

4. The device according to claim 1, wherein the soft adhesive layer has water absorption capacity of at least 15%.

5. The device according to claim 1, wherein the soft adhesive layer has water absorption capacity of at least 30%.

6. The device according to claim 1, wherein the second direction is horizontal when applied to the abdomen of a standing user.

7. The device according to claim 1, wherein the soft adhesive is anisotropic.

8. The device according to claim 1, wherein the backing layer is anisotropic.

9. The device according to claim 1, wherein the soft adhesive is moisture permeable and liquid impermeable.

10. The device according to claim 1, wherein the soft adhesive comprises a polyalkyleneoxide polymer and organosiloxane based cross-linked adhesive system.

11. The device according to claim 1, wherein the soft adhesive comprises ethylene vinyl acetate.

12. The device according to claim 1, wherein the soft adhesive comprises polyacrylate.

13. The device according to claim 1, wherein the soft adhesive comprises a cross-linked adhesive.

14. The device according to claim 13, wherein the cross-linked adhesive is selected from the group consisting of silicone adhesives and polyurethane adhesives.

15. The device according to claim 1, wherein the wafer comprises an anisotropic layer.

16. The device according to claim 15, wherein the anisotropic layer is a film, non-woven, fibre, knit, fabric, textile, laminate or foam.

17. The device according to claim 15, wherein the anisotropic layer is located between the backing layer and the soft adhesive layer.

18. The device according to claim 15, wherein the anisotropic layer is incorporated in the soft adhesive layer.

19. The device according to claim 15, wherein the anisotropic layer is located on the non-skin facing surface of the backing layer.

20. An ostomy collecting device for attachment to the body comprising:

a collecting pouch; and an adhesive wafer configured to be coupled with the collecting pouch and including a soft adhesive layer and a backing layer, the adhesive wafer having a thickness and defining a plane orthogonal to the thickness of the adhesive wafer, the adhesive wafer being stretchable in a first direction that is parallel to the plane of the adhesive wafer and the adhesive wafer being more stretchable in a second direction that is parallel to the plane of the adhesive wafer.

21. An ostomy collecting device for attachment to the body comprising:

a collecting pouch; and an adhesive wafer for adhering the collecting pouch to skin of a user, the adhesive wafer including a soft adhesive layer and a backing layer, the adhesive wafer having a thickness and defining a body orthogonal to the thickness of the adhesive wafer, the adhesive wafer being stretchable in a first direction that is parallel to the body of the adhesive wafer and stretchable in a second direction that is parallel to the body of the adhesive wafer, the adhesive wafer being more stretchable in the second direction than the first direction.

* * * * *